(12) United States Patent
Stojanovic-Susulic et al.

(10) Patent No.: US 7,790,671 B2
(45) Date of Patent: Sep. 7, 2010

(54) IMPLANTABLE PUMP FOR PROTEIN DELIVERY FOR OBESITY CONTROL BY DRUG INFUSION INTO THE BRAIN

(75) Inventors: Vedrana Stojanovic-Susulic, Princeton, NJ (US); Ramakrishna Venugopalan, Holliston, MA (US); Mark Cunningham, Kennett Square, PA (US)

(73) Assignee: Codman & Shurtleff, Inc., Raynham, MA (US)

( * ) Notice: Subject to any disclaimer, the term of this patent is extended or adjusted under 35 U.S.C. 154(b) by 618 days.

(21) Appl. No.: 11/245,653

(22) Filed: Oct. 7, 2005

(65) Prior Publication Data

US 2007/0082843 A1 Apr. 12, 2007

(51) Int. Cl.
*A61K 38/00* (2006.01)

(52) U.S. Cl. ........................................... 514/2

(58) Field of Classification Search .................. None
See application file for complete search history.

(56) References Cited

U.S. PATENT DOCUMENTS

| | | | |
|---|---|---|---|
| 5,034,229 A | 7/1991 | Magruder et al. | |
| 5,057,318 A | 10/1991 | Magruder | |
| 5,110,596 A | 5/1992 | Magruder et al. | |
| 5,286,789 A * | 2/1994 | Okrongly et al. | 525/54.11 |
| 5,368,588 A | 11/1994 | Bettinger | |
| 5,511,355 A | 4/1996 | Dingler et al. | |
| 5,532,347 A | 7/1996 | Cone et al. | |
| 5,703,220 A | 12/1997 | Yamada et al. | |
| 5,710,265 A | 1/1998 | Yamada et al. | |
| 5,713,847 A | 2/1998 | Howard | |
| 5,728,396 A | 3/1998 | Peery et al. | |
| 5,836,935 A | 11/1998 | Ashton | |
| 5,908,609 A | 6/1999 | Lee | |
| 5,932,779 A | 8/1999 | Lee et al. | |
| 5,976,109 A | 11/1999 | Heruth | |
| 5,985,305 A | 11/1999 | Peery et al. | |
| 6,113,938 A | 9/2000 | Chen et al. | |
| 6,132,420 A | 10/2000 | Dionne et al. | |
| 6,156,331 A | 12/2000 | Peery et al. | |
| 6,248,112 B1 | 6/2001 | Gambale et al. | |
| 6,283,949 B1 | 9/2001 | Roorda | |
| 6,375,978 B1 | 4/2002 | Kleiner et al. | |
| 6,395,292 B2 | 5/2002 | Peery | |
| 6,406,697 B1 * | 6/2002 | Capon et al. | 424/178.1 |
| 6,436,091 B1 | 8/2002 | Harper | |
| 6,447,522 B2 | 9/2002 | Gambale et al. | |
| 6,716,810 B1 | 4/2004 | Brennan et al. | |
| 2005/0186608 A1 | 8/2005 | Olsen et al. | |
| 2006/0084145 A1 | 4/2006 | Anderson et al. | |
| 2006/0105951 A1 * | 5/2006 | Cunningham et al. | 514/12 |
| 2006/0188496 A1 | 8/2006 | Bentz et al. | |

FOREIGN PATENT DOCUMENTS

| | | |
|---|---|---|
| WO | WO-97/47316 | 12/1997 |
| WO | WO-03/104761 | 12/2003 |
| WO | WO-2004/002424 | 1/2004 |
| WO | WO-2006/047535 | 5/2006 |
| WO | WO 2006047535 A2 * | 5/2006 |
| WO | WO-00/33658 | 6/2006 |

OTHER PUBLICATIONS

Pierroz et al., *Diabetes 51*: 1337-1345 (2002).
Fehm et al., J. Clin. Endo. Metabol. 86: 1144-1148 (2001).
Creighton, "Proteins—Structure and Molecular Properties," W.H. Freeman and Company, 2nd Ed. (1993).
Wold, F., "Posttranslational Protein Modifications: Perspectives and Prospects," Posttranslational Covalent Modifications of Proteins, pp. 1-12, B.C. Johnson, Ed., Academic Press, NY (1983).
Seifter et al., "Analysis for protein modifications and nonprotein cofactors," Meth Enzymol 182:626-646 (1990).
Rattan et al., "Protein synthesis: Posttranslational Modifications and Aging," Ann NY Acad Sci 663:48-62 (1992).
Fan et al., *Nature* 385:165-168 (1997).
Bays et. al., "Current and Investigational antiobesity agents and obesity therapeutic treatment targets", Obesity Research vol. 12, No. 8, p. 1197-1211, (2004).
McMinn et al, "Effect of intracerebroventricular alpha-MSH on food intake, adiposity, c-Fos induction, and neuropeptide expression", Am. J. of Physiology. Regulatory, Integrative and Comparative Physiology, vol. 279, No. 2, 2000, p. R695-R703.

* cited by examiner

*Primary Examiner*—Andrew D Kosar
(74) *Attorney, Agent, or Firm*—Nutter McClennen & Fish LLP

(57) ABSTRACT

Methods and compositions are provided for suppressing appetite by surgically implanting a drug infusion pump into a site in a subject, and delivering a stable suspension of an appetite suppressing agent a region in a central nervous system of the subject. The appetite suppressing agent binds to a target receptor on a neural cell in the central nervous system and modifies the receptor function to suppress appetite.

12 Claims, No Drawings

SEQUENCE LISTING

```
<160> NUMBER OF SEQ ID NOS: 18

<210> SEQ ID NO 1
<211> LENGTH: 39
<212> TYPE: DNA
<213> ORGANISM: Homo sapiens

<400> SEQUENCE: 1
tcctactcca tggagcactt ccgctggggc aagccggtg                          39

<210> SEQ ID NO 2
<211> LENGTH: 13
<212> TYPE: PRT
<213> ORGANISM: Homo sapiens

<400> SEQUENCE: 2

Ser Tyr Ser Met Glu His Phe Arg Trp Gly Lys Pro Val
1               5                   10

<210> SEQ ID NO 3
<211> LENGTH: 12
<212> TYPE: DNA
<213> ORGANISM: Homo sapiens

<400> SEQUENCE: 3
```

-continued cattttcgct gg                                                              12

<210> SEQ ID NO 4
<211> LENGTH: 4
<212> TYPE: PRT
<213> ORGANISM: Homo sapiens

<400> SEQUENCE: 4

His Phe Arg Trp
1

<210> SEQ ID NO 5
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
agctatagct gcgaacattt tcgctggtgc aaaccggtg                                  39

<210> SEQ ID NO 6
<211> LENGTH: 13
<212> TYPE: PRT
<213> ORGANISM: Artificial Sequence
<220> FEATURE:
<223> OTHER INFORMATION: Synthetic a-MSH peptide

<400> SEQUENCE: 6

Ser Tyr Ser Cys Glu His Phe Arg Trp Cys Lys Pro Val
1               5                   10

<210> SEQ ID NO 7
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 7
agctattgca tggaacattt tcgctggtgc aaaccggtg                                  39

<210> SEQ ID NO 8
<211> LENGTH: 13
<212> TYPE: PRT
<213> ORGANISM: Artificial Sequence
<220> FEATURE:
<223> OTHER INFORMATION: Synthetic a-MSH peptide

<400> SEQUENCE: 8

Ser Tyr Cys Met Glu His Phe Arg Trp Cys Lys Pro Val
1               5                   10

<210> SEQ ID NO 9
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 9
agctgcagca tggaacattt tcgctggtgc aaaccggtg                                  39

<210> SEQ ID NO 10
<211> LENGTH: 13

```
<212> TYPE: PRT
<213> ORGANISM: Artificial Sequence
<220> FEATURE:
<223> OTHER INFORMATION: Synthetic a-MSH peptide

<400> SEQUENCE: 10

Ser Cys Ser Met Glu His Phe Arg Trp Cys Lys Pro Val
1               5                   10

<210> SEQ ID NO 11
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 11
tgctatagca tggaacattt tcgctggggc tgcccggtg                              39

<210> SEQ ID NO 12
<211> LENGTH: 13
<212> TYPE: PRT
<213> ORGANISM: Artificial Sequence
<220> FEATURE:
<223> OTHER INFORMATION: Synthetic a-MSH peptide

<400> SEQUENCE: 12

Cys Tyr Ser Met Glu His Phe Arg Trp Gly Cys Pro Val
1               5                   10

<210> SEQ ID NO 13
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 13
tttcattgga tg                                                          12

<210> SEQ ID NO 14
<211> LENGTH: 4
<212> TYPE: PRT
<213> ORGANISM: Artificial Sequence
<220> FEATURE:
<223> OTHER INFORMATION: Synthetic construct

<400> SEQUENCE: 14

Phe His Trp Met
1

<210> SEQ ID NO 15
<211> LENGTH: 777
<212> TYPE: DNA
<213> ORGANISM: Artificial Sequence
<220> FEATURE:
<223> OTHER INFORMATION: Synthetic oligonucleotide

<400> SEQUENCE: 15
tcctactcca tggagcactt ccgctggggc aagccggtgg gatccggtgg aggctccggt      60 acctagtca ccgtctcctc agagcccaaa tcttgtgaca aaactcacac gtgcccaccg      120
tgcccagcac ctgaactcct ggggggaccg tcagtcttcc tcttcccccc aaaacccaag     180
gacaccctca tgatctcccg gacccctgag gtcacatgcg tggtggtgga cgtgagccac     240
gaagaccctg aggtcaagtt caactggtac gtggacggcg tggaggtgca taatgccaag     300
```

-continued

```
acaaagccgc gggaggagca gtacaacagc acgtaccggg tggtcagcgt cctcaccgtc    360
ctgcaccagg actggctgaa tggcaaggag tacaagtgca aggtctccaa caaagccctc    420
ccagccccca tcgagaaaac catctccaaa gccaaagggc agccccgaga accacaggtg    480
tacaccctgc ccccatcccg ggatgagctg accaagaacc aggtcagcct gacctgcctg    540
gtcaaaggct tctatcccag cgacatcgcc gtggagtggg agagcaatgg gcagccggag    600
aacaactaca agaccacgcc tcccgtgctg gactccgacg gctccttctt cctctacagc    660
aagctcaccg tggacaagag caggtggcag caggggaacg tcttctcatg ctccgtgatg    720
catgaggctc tgcacaacca ctacacgcag aagagcctct ccctgtctcc gggtaaa      777
```

<210> SEQ ID NO 16
<211> LENGTH: 259
<212> TYPE: PRT
<213> ORGANISM: Artificial Sequence
<220> FEATURE:
<223> OTHER INFORMATION: Synthetic a-MSH mimetibody-without secretory
signal

<400> SEQUENCE: 16

```
Ser Tyr Ser Met Glu His Phe Arg Trp Gly Lys Pro Val Gly Ser Gly
1               5                   10                  15

Gly Gly Ser Gly Thr Leu Val Thr Val Ser Ser Glu Pro Lys Ser Cys
            20                  25                  30

Asp Lys Thr His Thr Cys Pro Pro Cys Pro Ala Pro Glu Leu Leu Gly
        35                  40                  45

Gly Pro Ser Val Phe Leu Phe Pro Pro Lys Pro Lys Asp Thr Leu Met
    50                  55                  60

Ile Ser Arg Thr Pro Glu Val Thr Cys Val Val Val Asp Val Ser His
65                  70                  75                  80

Glu Asp Pro Glu Val Lys Phe Asn Trp Tyr Val Asp Gly Val Glu Val
                85                  90                  95

His Asn Ala Lys Thr Lys Pro Arg Glu Glu Gln Tyr Asn Ser Thr Tyr
            100                 105                 110

Arg Val Val Ser Val Leu Thr Val Leu His Gln Asp Trp Leu Asn Gly
        115                 120                 125

Lys Glu Tyr Lys Cys Lys Val Ser Asn Lys Ala Leu Pro Ala Pro Ile
    130                 135                 140

Glu Lys Thr Ile Ser Lys Ala Lys Gly Gln Pro Arg Glu Pro Gln Val
145                 150                 155                 160

Tyr Thr Leu Pro Pro Ser Arg Asp Glu Leu Thr Lys Asn Gln Val Ser
                165                 170                 175

Leu Thr Cys Leu Val Lys Gly Phe Tyr Pro Ser Asp Ile Ala Val Glu
            180                 185                 190

Trp Glu Ser Asn Gly Gln Pro Glu Asn Tyr Lys Thr Thr Pro Pro
        195                 200                 205

Val Leu Asp Ser Asp Gly Ser Phe Phe Leu Tyr Ser Lys Leu Thr Val
    210                 215                 220

Asp Lys Ser Arg Trp Gln Gln Gly Asn Val Phe Ser Cys Ser Val Met
225                 230                 235                 240

His Glu Ala Leu His Asn His Tyr Thr Gln Lys Ser Leu Ser Leu Ser
                245                 250                 255

Pro Gly Lys
```

<210> SEQ ID NO 17
<211> LENGTH: 843
<212> TYPE: DNA
<213> ORGANISM: Artificial Sequence
<220> FEATURE:
<223> OTHER INFORMATION: Synthetic oligonucleotide

<400> SEQUENCE: 17

```
atggcttggg tgtggacctt gctattcctg atggcggccg cccaaagtat acaggcccag      60
atccagtcct actccatgga gcacttccgc tggggcaagc cggtgggatc cggtggaggc     120
tccggtacct tagtcaccgt ctcctcagag cccaaatctt gtgacaaaac tcacacgtgc     180
ccaccgtgcc cagcacctga actcctgggg ggaccgtcag tcttcctctt ccccccaaaa     240
cccaaggaca cccctcatga tctcccggac cctgaggtca catgcgtggt ggtggacgtg     300
agccacgaag accctgaggt caagttcaac tggtacgtgg acggcgtgga ggtgcataat     360
gccaagacaa agccgcggga ggagcagtac aacagcacgt accgggtggt cagcgtcctc     420
accgtcctgc accaggactg gctgaatggc aaggagtaca agtgcaaggt ctccaacaaa     480
gccctcccag cccccatcga gaaaaccatc tccaaagcca agggcagccc cgagaaccca     540
caggtgtaca ccctgccccc atcccgggat gagctgacca agaaccaggt cagcctgacc     600
tgcctggtca aaggcttcta tcccagcgac atcgccgtgg agtgggagag caatgggcag     660
ccggagaaca actacaagac cacgcctccc gtgctggact ccgacggctc cttcttcctc     720
tacagcaagc tcaccgtgga caagagcagg tggcagcagg ggaacgtctt ctcatgctcc     780
gtgatgcatg aggctctgca caaccactac acgcagaaga gcctctccct gtctccgggt     840
aaa                                                                   843
```

<210> SEQ ID NO 18
<211> LENGTH: 281
<212> TYPE: PRT
<213> ORGANISM: Artificial Sequence
<220> FEATURE:
<223> OTHER INFORMATION: Synthetic a-MSH mimetibody-with secretory
      signal

<400> SEQUENCE: 18

```
Met Ala Trp Val Trp Thr Leu Leu Phe Leu Met Ala Ala Ala Gln Ser
1               5                   10                  15

Ile Gln Ala Gln Ile Gln Ser Tyr Ser Met Glu His Phe Arg Trp Gly
            20                  25                  30

Lys Pro Val Gly Ser Gly Gly Gly Ser Gly Thr Leu Val Thr Val Ser
        35                  40                  45

Ser Glu Pro Lys Ser Cys Asp Lys Thr His Thr Cys Pro Pro Cys Pro
    50                  55                  60

Ala Pro Glu Leu Leu Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Lys Phe Asn Trp Tyr
            100                 105                 110

Val Asp Gly Val Glu Val His Asn Ala Lys Thr Lys Pro Arg Glu Glu
        115                 120                 125

Gln Tyr Asn Ser Thr Tyr Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160
```

```
Ala Leu Pro Ala Pro Ile Glu Lys Thr Ile Ser Lys Ala Lys Gly Gln
            165                 170             175

Pro Arg Glu Pro Gln Val Tyr Thr Leu Pro Pro Ser Arg Asp Glu Leu
            180                 185             190

Thr Lys Asn Gln Val Ser Leu Thr Cys Leu Val Lys Gly Phe Tyr Pro
        195                 200             205

Ser Asp Ile Ala Val Glu Trp Glu Ser Asn Gly Gln Pro Glu Asn Asn
        210             215             220

Tyr Lys Thr Thr Pro Pro Val Leu Asp Ser Asp Gly Ser Phe Phe Leu
225                 230             235                 240

Tyr Ser Lys Leu Thr Val Asp Lys Ser Arg Trp Gln Gln Gly Asn Val
                245             250                 255

Phe Ser Cys Ser Val Met His Glu Ala Leu His Asn His Tyr Thr Gln
            260             265             270

Lys Ser Leu Ser Leu Ser Pro Gly Lys
        275             280
```

IMPLANTABLE PUMP FOR PROTEIN DELIVERY FOR OBESITY CONTROL BY DRUG INFUSION INTO THE BRAIN

FIELD OF THE INVENTION

The present invention relates to using implantable drug infusion pumps and methods for delivering appetite suppressing agents to the central nervous system.

BACKGROUND OF THE INVENTION

Recent studies have indicated that between a third and a half of all Americans are either overweight or obese (have a Body Mass Index (BMI) of greater than 25 kg/m$^2$). Increases in caloric intake coupled with declines in exercise levels among the population have set the stage for a problem of epidemic proportions. The importance of addressing this problem and ultimately treating obesity is emphasized by the fact that this disease is either the underlying cause, or a risk factor, for developing diseases such as type II diabetes, congestive heart failure, osteoarthritis and sleep apnea among others.

Currently, the primary treatment for obesity typically involves behavioral change involving dietary restraints to reduce caloric intake coupled with aerobic and anaerobic exercise. Several dietary supplement drugs or other ingestible preparations are also used as appetite suppressors. In general, these techniques tend to produce only a temporary effect.

Recently, melanocortin receptors have been found to play a major role in the regulation of energy balance and obesity in humans as well as other mammals. In fact, weight loss has been found to result from the pharmacological stimulation of melanocortin system activity. In rodents pharmacological stimulation of certain melanocortn receptors has lead to decreased food intake, increased energy expenditure and weight loss (Pierroz et al., *Diabetes* 51: 1337-1345 (2002)). In humans intranasal administration of Alpha-melanocyte stimulating hormone (alpha-MSH), a 13 amino acid peptide hormone, in non-obese men resulted in decreased body weight due to the loss of fat mass. (Fehm et al., *J. Clin. Endo. Metabol.* 86: 1144-1148 (2001)).

To date, melanocortin receptor binding peptides such as alpha-MSH, have had limited use as pharmaceuticals due to their extremely short serum half-life. In addition, recent efforts to develop specific small molecule agonists of alpha-MSH have been slow; none of these compounds have advanced into the clinic.

Accordingly, a need exists for a more effective therapy for obesity and in particular more effective methods of delivering modulators of melanocorin system activity to subjects are needed.

SUMMARY OF THE INVENTION

The invention provides systems, methods and compositions for suppressing appetite as a way to regulate body weight and obesity. In particular, the invention pertains to suppressing appetite by administering at least one appetite suppressing agent that modulates the melanocortin system, an important pathway involved in weight gain and obesity.

The present invention involves suppressing appetite in a subject by implanting a drug infusion pump into a site in the subject. A stable suspension of an appetite suppressing agent can then delivered to region in a central nervous system of the subject, e.g., a region of the brain. The appetite suppressing agent can bind to a target receptor associated with appetite that is present on a neural cell, and modify the function of a receptor, to thereby suppress appetite.

In another aspect, the invention pertains to a method for ameliorating obesity in a subject by surgically implanting a drug infusion pump into a site in the subject. A stable suspension of a melanocortin, such as a melanocyte-stimulating hormone (MSH), can then be delivered to a site in the central nervous system of the subject. The melanocortin can bind to a melanocortin receptor that is present on a neural cell, and modify the melanocortin receptor function to suppress appetite, to thereby ameliorate obesity.

DETAILED DESCRIPTION OF THE INVENTION

Introduction

Certain exemplary embodiments of the invention will now be described to provide an overall understanding of the principles of the structure, function, manufacture, and use of the methods and compositions disclosed herein. Those skilled in the art will understand that the methods and compositions specifically described herein are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

In particular, the invention pertains to suppressing appetite by administering an appetite suppressing agent that modulates the melanocortin system, an important pathway involved in weight gain. Melanocortins and melanocortin receptors play a major role in the regulation of overall energy balance and obesity in humans.

In one aspect of the invention, the appetite suppressing agent is delivered to a central nervous system target site (e.g., the intrathecal space, the brain) by an implantable drug infusion pump.

Definitions

Various terms relating to the biological molecules of the present invention are used throughout the specification and claims.

"Obesity" means the abnormal accumulation of body fat, also referred to as adipose tissue, above a medically relevant threshold, such as a BMI exceeding 27 kg/m$^2$. The term is specifically meant to include subjects that have classically been categorized as both "overweight" and "obese."

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein.

"Polynucleotide" generally refers to any polyribonucleotide or polydeoxyribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA.

The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the gene-encoded amino acids. "Polypeptides" include amino acid sequences modified either by natural processes, such as posttranslational processing, or by chemical modification techniques that are well known in the art. Such modifications are well described in basic texts and in more detailed monographs; as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched circular polypeptides may result from posttranslation natural processes or may be made by synthetic methods.

Modifications include acetylation, acylation, ADP-ribosylation, amidation, covalent attachment of various moiety groups, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cystine, formation of pyroglutamate, formylation, gamma-carboxylation, glycosylation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. See, for instance, Proteins—Structure And Molecular Properties, 2nd Ed., T. E. Creighton, W. H. Freeman and Company, New York, 1993 and Wold, F., "Posttranslational Protein Modifications: Perspectives and Prospects, pgs. 1-12 in "Posttranslational Covalent Modification Of Proteins", B, C. Johnson, Ed., Academic Press, New York, 1983; Seifter et al., "Analysis for protein modifications and nonprotein cofactors", *Meth Enzynol* 182: 626-646 (1990) and Rattan et al., "Protein Synthesis: Posttranslational Modifications and Aging", *Ann NY Acad Sci* 663:48-62 (1992).

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical.

A variant and reference polypeptide may differ in amino acid sequence by one or more substitutions, additions, and deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis. For instance, a conservative amino acid substitution may be made with respect to the amino acid sequence encoding the polypeptide.

A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "substantially the same" refers to nucleic acid or amino acid sequences having sequence variations that do not materially affect the nature of the protein (i.e. the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

With respect to oligonucleotide constructs, but not limited thereto, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide construct with a substantially complementary sequence contained within a single-stranded DNA or RNA molecule of the invention, to the substantial exclusion of hybridization of the oligonucleotide with single-stranded nucleic acids of non-complementary sequence.

The term "substantially pure" refers to a "preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate to the compound of interest (e.g. chromatographic methods, agarose or polyacrylamide gel electrophoresis, HPLC analysis, and the like).

The term "expression cassette" refers to a nucleotide sequence that contains at least one coding sequence along with sequence elements that direct the initiation and termination of transcription. An expression cassette may include additional sequences, including, but not limited to promoters, enhancers, sequences involved in post-transcriptional or post-translational processes, as well as appropriate terminator sequences.

A "coding sequence" or "coding region" refers to a nucleic acid molecule having sequence information necessary to produce a gene product, when the sequence is expressed.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g., enhancers and regulators) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The term "nucleic acid construct" or "DNA construct" is sometimes used to refer to a coding sequence or sequences operably linked to appropriate regulatory sequences and inserted into a vector for transforming a cell, in vitro or in vivo. This term may be used interchangeably with the term "transforming DNA". Such a nucleic acid construct may contain a coding sequence for a gene product of interest, along with a selectable marker gene and/or a reporter gene.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The term "DNA construct", as defined above, is also used to refer to a heterologous region, particularly one constructed for use in transformation of a cell. A cell has been "transformed" or "transfected" or "transduced" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

"Delivery of a therapeutic element or agent" may be carried out through a variety of means, such as by using parenteral delivery methods such as intravenous and subcutaneous injection, and the like. Such methods are known to those of skill in the art of drug delivery, and are further described herein in the sections regarding pharmaceutical preparations and treatment.

By a "therapeutically effective amount" is meant an amount of the polynucleotide or protein of, or fragment thereof, that when administered to a subject is effective to bring about a desired effect (e.g., a decrease of body fat) within the subject.

Receptors, Peptides and Polynucleotides

Melanocortin receptors are members of the G-protein coupled receptor class. To date, five melanocortin receptors have been identified, each having a unique tissue expression pattern. Examples of melanocortin receptors include, but are not limited to, melanocortin-1 receptor (MC1R), melanocortin-2 receptor (MC2R), melanocortin-3 receptor (MC3R), melanocortin-4 receptor (MC4R), and melanocortin-5 receptor (MC5R).

Details of melanocortin receptor genes and proteins are available, for example in, U.S. Pat. Nos. 5,703,220 and 5,710,265 to Yamada et al.; U.S. Pat. No. 5,532,347 to Cone et al.; and PCT Publication WO 97/47316 and U.S. Pat. Nos. 5,908,609 and 5,932,779 to Lee et al.; which describe known melanocortin receptors and the genes encoding such receptors. Each of these patents and PCT publication is incorporated herein by reference in its entirety.

Melanocortins are cleavage products of pro-opiomelanocortin (POMC). Examples of melanocortins include, but are not limited to, adrenocorticotrophin (ACTH), alpha-melanocyte stimulating hormone (α-MSH), beta-melanocyte stimulating hormone (β-MSH), gamma-melanocyte stimulating hormone (γ-MSH), and beta-endorphin.

In one embodiment, the melanocortin is alpha-melanocyte stimulating hormone ((α-MSH), a 13 amino acid peptide hormone that is an important component of the melanocortin system encoding by the nucleic acid sequence TCCTACTCCA TGGAGCACTT CCGCTGGGGC AAGC-CGGTG (SEQ ID NO: 1) and having the amino acid sequence SYSMEHFRWGKPV (SEQ ID NO: 2). Alpha-MSH is produced by the proteolytic processing of pro-opiomelanocortin released by the pituitary gland. Alpha-MSH binds with high affinity to the melanocortin-4 receptor (MC4R), but also binds melanocortin-3 receptor (MC3R) and melanocortin-5 receptor (MC5R). MC4R is a G-coupled protein receptor found in the brain which, when stimulated by alpha-MSH binding, causes decreased food intake and increased fat oxidation. Ultimately, stimulation of melanocortin receptors such as MC4R results in weight loss.

Mimetibodies

Also included within the scope of the invention are homologs of α-MSH, mimetics (peptide or non-peptide) of α-MSH, fusion proteins comprising α-MSH, conjugates of α-MSH, and any pharmaceutical salts of α-MSH. Exemplary conjugates of α-MSH peptides are those conjugated to antibodies or antibody fragments, also referred to as mimetibodies.

The present invention provides polypeptides having the properties of binding a melanocortin receptor and mimicking different isotypes of antibody immunoglobulin molecules such as IgA, IgD, IgE, IgG, or IgM, and any subclass thereof, such as $IgA_1$, $IgA_2$, $IgG_1$, $IgG_2$, $IgG_3$ or $IgG_4$, or combinations thereof, herein after generally referred to as "mimetibodies." In some embodiments, the mimetibody polypeptides of the invention contain an alpha melanocyte stimulating hormone peptide (alpha-MSH) sequence and are designated melanocortin receptor binding alpha-MSH mimetibody. Such alpha-MSH mimetibody polypeptides can bind melanocortin receptor 4 (MC4R) and, with equal and lower affinity, for MC3R and MC5R respectively. One result of such melanocortin receptor binding can be the stimulation or inhibition of melanocortin receptor activity. Stimulation can cause weight loss while inhibition may cause weight gain.

In one embodiment the polypeptides of the invention have the generic formula (I):

$$(Mp-Lk-V2-Hg-C_H2-C_H3)_{(t)} \quad (I)$$

where Mp is a melanocortin receptor binding molecule, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region and t is independently an integer of 1 to 10.

As used herein, "melanocortin receptor binding molecule" means a molecule, which can bind at least one melanocortin receptor such as MC1R, MC2R, MC3R, MC4R, and MC5R. A given peptide chain is a "melanocortin receptor" if it has at least 85% amino acid sequence identity to a known melanocortin receptor sequence or the mature form of a known melanocortin receptor and can function as a G-protein coupled receptor. Percent identity between two peptide chains can be determined by pairwise alignment using the default settings of the AlignX module of Vector NTI v.9.0.0 (Invitrogen Corp., Carslbad, Calif.). An exemplary melanocortin receptor binding molecule is the 13 amino acid alpha-MSH peptide having the nucleic acid sequence TCCTACTCCA TGGAGCACTT CCGCTGGGGC AAGC-CGGTG (SEQ ID NO: 1) and the amino acid sequence SYSMEHFRWGKPV (SEQ ID NO: 2). Other melanocortin receptor binding molecules include biologically active fragments of SEQ ID NO: 2 and other amino acid sequences that can bind a melanocortin receptor. The term "biologically active fragment" as used herein, refers to a portion of an alpha-MSH peptide that can bind to a melanocortin receptor such as MC4R. The peptide sequence HFRW (SEQ. ID. NO. 4) encoded by DNA sequence CATTTTCGCT GG (SEQ. ID. NO. 3) is an exemplary "biologically active fragment" of the alpha-MSH peptide sequence SYSMEHFRWGKPV (SEQ ID NO:2). The HFRW fragment has been incorporated into the structure of the synthetic melanocortin receptor activator molecule melanotan II (MTII) (Fan et al., Nature 385: 165-168 (1997)).

Incorporation of melanocortin receptor binding molecules in the mimetibody polypeptides of the invention provides for binding to melanocortin receptors with a wide range of affinities. The mimetibody polypeptides of the invention may bind a melanocortin receptor with a $K_d$ less than or equal to about $10^{-7}$, $10^{-8}$, $10^{-9}$, $10^{-10}$, $10^{-11}$ or $10^{-12}$ M. The range of obtained IC50 values for aMSH peptide, MTII peptide and aMSHMMB were 260-400 nM, 5-30 nM and 200-300 nM respectively. The affinity of a mimetibody polypeptide for a melanocortin receptor can be determined experimentally using any suitable method. Such methods may utilize Biacore or KinExA instrumentation, ELISA or competitive binding assays. Mimetibody polypeptides binding specific melanocortin receptors with a desired affinity can be selected from libraries of variants or fragments by techniques known to those skilled in the art.

An alpha-MSH peptide having the amino acid sequence shown in SEQ ID NO: 2 may be modified to obtain other melanocortin receptor binding molecules. Such modifications may comprise the incorporation of C-$[X]_n$-C motifs into the peptide to conformationally constrain the peptide through the formation of disulfide bonds. In a C-$[X]_n$-C motif, C is a cysteine residue, X is a amino acid residues and n is an integer necessary to achieve the required conformational constraint. In this instance n can be as little as 1 residue and as high as 50. Exemplary C-$[X]_n$-C modified peptide sequences are shown below:

```
                                        (SEQ ID NO:5)
AGCTATAGCT GCGAACATTT TCGCTGGTGC AAACCGGTG (SEQ ID NO:6)
SER TYR SER CYS GLU HIS PHE ARG TRP CYS LYS PRO

VAL (SEQ ID NO:7)
AGCTATTGCA TGGAACATTT TCGCTGGTGC AAACCCGTG (SEQ ID NO:8)
SER TYR CYS MET GLU HIS PHE ARG TRP CYS LYS PRO

VAL (SEQ ID NO:9)
AGCTGCAGCA TGGAACATTT TCGCTGGTGC AAACCGGTG (SEQ ID NO:10)
SER CYS SER MET GLU HIS PHE ARG TRP CYS LYS PRO

VAL (SEQ ID NO:11)
TGCTATAGCA TGGAACATTT TCGCTGGGGC TGCCCGGTG (SEQ ID NO:12)
CYS TYR SER MET GLU HIS PHE ARG TRP GLY CYS PRO

VAL
```

The modification may also comprise the incorporation of a Wa-$[X]_n$-Wa motif into the peptide to conformationally constrain the peptide through the formation of a tryptophan zipper. In a Wa-$[X]_n$-Wa motif W is tryptophan residue, X is an amino acid, a is an integer usually 2, but can be from 1 to 10, and n is an integer necessary to achieve the required conformational constraint. In this instance n can be as little a 1 residue and as high as 50. Further, the sequence HFRW (SEQ ID NO: 4) present in the alpha-MSH peptide may also be modified by substituting any residue in this sequence with any one of F, H, W and M; for example, HFRW (SEQ ID NO: 4) can be substituted to FHWM (SEQ ID NO: 14) coded by the nucleic acid sequence TTTCATTGGATG (SEQ ID NO: 13).

In the polypeptides of the invention, the linker portion (Lk) provides structural flexibility by allowing the mimetibody to have alternative orientations and binding properties. Exemplary linkers include non-peptide chemical linkages or one to 20 amino acids linked by peptide bonds, wherein the amino acids are selected from the 20 naturally occurring amino acids or other amino acids (e.g. D-amino acids, non-naturally occurring amino acids, or rare naturally occurring amino acids). The linker portion can include a majority of amino acids that are sterically unhindered, such as glycine, alanine and serine and can include GS, poly GS or any combination or polymer thereof. Other exemplary linkers within the scope of the invention may be longer than 20 residues and may include residues other than glycine, alanine and serine In the mimetibodies used in the invention, V2 is a portion of a carboxy terminal domain of an immunoglobulin variable region such as a heavy chain variable region; Hg is a portion of the hinge domain of an immunoglobulin variable region such as a heavy chain variable region.; $C_H2$ is an immunoglobulin heavy chain $C_H2$ constant region; $C_H3$ is an immunoglobulin heavy chain $C_H3$ constant region. It will be recognized by those skilled in the art that the $C_H3$ region of the polypeptides of the invention may have its C-terminal amino acid cleaved off when expressed in certain recombinant systems.

In the mimetibody polypeptides used in the invention Hg, $C_H2$ or $C_H3$ may be of the $IgG_1$ or $IgG_4$ subclass. A sequence is of the $IgG_1$ or $IgG_4$ subclass if it is formed or developed from a γ1 or γ4 heavy chain respectively. A given peptide chain is a γ1 or γ4 heavy chain if it is at least 80% identical to a known γ1 or γ4 heavy chain sequence of a given species. Percent identity between two peptide chains can be determined by pairwise alignment using the default settings of the AlignX module of Vector NTI v.9.0.0 (Invitrogen Corp., Carlsbad, Calif.).

In the mimetibody polypeptides used in the invention Hg, $C_H2$ or $C_H3$ may individually be of the $IgG_1$ or $IgG_4$ subclass. The mimetibodies of the invention may also comprise combinations of Hg, $C_H2$ or $C_H3$ elements from each subclass For example, Hg may be of the $IgG_4$ subclass while $C_H2$ and $C_H3$ are of the $IgG_1$ subclass. Alternatively, Hg, $C_H2$ and $C_H3$ may all of the $IgG_4$ or $IgG_1$ subclass. The $IgG_1$ and $IgG_4$ subclasses differ in the number of cysteines in the hinge region. Most IgG type antibodies, such as $IgG_1$, are homodimeric molecules made up of two identical heavy (H) chains and two identical light (L) chains, typically abbreviated $H_2L_2$. Thus, these molecules are generally bivalent with respect to antigen binding due to the formation of inter-heavy chain disulfide bonds and both antigen binding (Fab) arms of the IgG molecule have identical binding specificity. $IgG_4$ isotype heavy chains, in contrast, contain a CPSC motif in their hinge regions capable of forming either inter- or intra-heavy chain disulfide bonds, i.e., the two Cys residues in the CPSC motif may disulfide bond with the corresponding Cys residues in the other H chain (inter) or the two Cys residues within a given CPSC motif may disulfide bond with each other (intra). Since the HL pairs in those $IgG_4$ molecules with intra-heavy chain bonds in the hinge region are not covalently associated with each other, they may dissociate into HL monomers that then reassociate with HL monomers derived from other $IgG_4$ molecules forming bispecific, heterodimeric $IgG_4$ molecules. In vivo isomerase enzymes may facilitate this process. In a bispecific IgG antibody the two Fab "arms" of the antibody molecule differ in the epitopes that they bind. Substituting Ser residues in the hinge region of $IgG_4$ with Pro results in "$IgG_1$-like behavior," i.e., the molecules form stable disulfide bonds between heavy chains and therefore, are not susceptible to HL exchange with other $IgG_4$ molecules.

The mimetibody polypeptides of the invention may be made more $IgG_4$-like, or $IgG_1$-like by the modification of sites which are involved in disulfide bond formation and are present in the Hg—$C_H2$-$C_H3$ portion of the mimetibody polypeptides. Such sites may be modified by removal, deletion, insertion or substitution with other amino acids. Typically, the cysteine residues present in disulfide bond associated motifs are removed or substituted. Removal of these sites may avoid covalent disulfide bonding with other cysteine-containing proteins present in the mimetibody producing host cell or intra-heavy chain disulfide bonding in $IgG_4$-based constructs while still allowing for noncovalent dimerization of mimetibody Hg—$C_H2$-$C_H3$ domains. Modification of such sites can permit the formation of bispecific mimetibody polypeptides with two different M portions or prevent the formation of such bispecific species The $IgG_1$ and $IgG_4$ subclasses also differ in their ability to mediate complement dependent cytotoxicity (CDC) and antibody-dependent cellular cytotoxicity (ADCC). CDC is the lysing of a target cell in the presence of complement. The complement activation pathway is initiated by the binding of the first component of the complement system (Clq) to a molecule complexed with a cognate antigen. $IgG_1$ is a strong inducer of the complement cascade and subsequent CDC activity, while $IgG_4$ has little complement-inducing activity. ADCC is a cell-mediated process in which nonspecific cytotoxic cells that express Fc receptors (FcRs) involved in ADCC (e.g., natural killer (NK) cells, neutrophils, and macrophages) recognize bound antibody on a target cell and subsequently cause lysis of the target cell. The $IgG_1$ subclass binds with high affinity to Fc receptors involved in ADCC and contributes to ADCC, while $IgG_4$ binds only weakly to such receptors and has little ADCC inducing activity. The relative inability of $IgG_4$ to activate effector functions such as ADCC is desirable since delivery of the mimetibody polypeptide to cells without cell killing is possible.

The CDC and ADCC activity of the mimetibody polypeptides of the invention may be modified by altering sites involved in CDC and ADCC present in the Hg—$C_H2$-$C_H3$ portion of the mimetibody polypeptide. Such sites may be modified by removal, deletion, insertion or substitution with other amino acids. In the mimetibodies of the invention sites involved in CDC, such as the Clq binding site, are typically removed or otherwise modified to minimize CDC activity. Additionally, Fc receptor binding sites involved in ADCC can also be similarly modified in the mimetibodies of the invention. In general, such modification will remove Fc receptor binding sites involved in ADCC activity from the mimetibodies of the invention. The substitution of Leu residues with Ala residues in the $C_H2$ portion of the polypeptides of the invention is one example of a modification which can minimize ADCC activity in the polypeptides of the invention. The $C_H2$ amino acid sequence.

Antibodies of both the $IgG_4$ and $IgG_1$ isotypes contain FcRn salvage receptor binding sites. The FcRn salvage receptor helps maintain IgG antibody levels in the body by recycling or transporting IgG type antibodies across enodothelial cell layers such as those lining the inside of body cavities and blood vessels. The FcRn salavage receptor does this by binding IgGs that have entered endothelial cells by nonspecific pinocytosis and preventing these IgG antibody molecules from being degraded in the lysosome of the cell. The result of such FcRn receptor activity is that the serum half-life of a molecule with an FcRn binding site is extended relative to an otherwise identical molecule lacking such a site.

It is desirable that the Hg—$C_H2$-$C_H3$ portion of the mimetibodies of the invention contain a FcRn binding site at the junction of the $C_H2$ and $C_H3$ regions. It is expected that such FcRn sites will increase the serum half-life of the mimetibodies of the invention as well as improve other pharmacokinetic properties relative to a melanocortin receptor binding molecule, such as alpha-MSH alone. In the mimetibodies of the invention FcRn sites may be modified or added by removal, deletion, insertion or substitution of amino acids. Typically, such modifications are used to improve the binding of a given site to the FcRn.

Antibodies with different isotypes, such as $IgG_4$ and $IgG_1$, may contain glycosylation sites. Glycosylation of these sites can alter the properties and activites of antibody molecules. Antibody molecules may be N-glycosylated or O-glycosylated. N-glycosylation of antibody amino acid residue side chains containing nitrogen atoms (e.g., Asn) can modulate antibody Fc effector functions such as ADCC by conferring a cytolytic activity to N-glycosylated antibody molecules. This ADCC associated cytolytic activity causes the lysis of cells effected by such N-glycosylated antibodies. Alternatively, an antibody molecule may be O-glycosylated by modification of amino acid residue side chains containing oxygen atoms (e.g., Ser or Thr). O-glycosylation can decrease the serum half-life of an antibody molecule through increased lectin mediated clearance of O-glycosylated antibody molecules from the serum. Additionally, O-glycosylation can cause undesirable increases in antibody heterogeneity due to differing extents of O-glycosylation between various antibody molecules. Lastly, both O-glycosylation and N-glycosylation can alter the structure dependent properties of antibody molecules such as binding affinity and immunogenicity.

Like the antibody molecules they mimic, the mimetibody polypeptides of the invention may also be post-translationally modified by N-glycosylation and O-glycosylation. In most instances, it is desirable to limit the N-glycosylation of the mimetibodies of the invention to minimize cytolytic activity. N-glycosylation can be limited by the removal or substitution of amino acid residues, such as Asn, which are typically N-glycosylated. It is also desirable to limit mimetibody O-glycosylation to minimize lectin-mediated clearance, mimetibody heterogeneity and the alteration of structure dependent mimetibody properties such as binding affinity and immunogenicity. One way to minimize O-linked glycosylation in the mimetibodies of the invention is to substitute Ala residues for Thr residues in the V2 portion of the polypeptides of the invention.

The monomeric structure Mp-Lk-V2-Hg—$C_H2$-$C_H3$ of the mimetibody polypeptides of the invention can be linked to "t" other monomers where t is an integer from 1 to 10. Such linking can occur through non-covalent interactions or covalent linkages such as a Cys-Cys disulfide bond. In this way multimeric structures such as dimers and higher order multimers of the polypeptides of the invention can be formed. It is expected that dimerization of the polypeptides of the invention will increase the affinity of these polypeptides to melanocortin receptors such as MC4R. The term "multimers" as used herein means molecules that have quaternary structure and are formed by the association of two or more subunits.

The polypeptides of the invention can optionally comprise at the amino terminus, a amino terminal portion of an immunoglobulin variable region, designated V1 as shown in Formula II:

$$(V1\text{-}Mp\text{-}Lk\text{-}V2\text{-}Hg\text{—}C_H2\text{-}C_H3)_{(t)} \quad \text{(II)}$$

The polypeptides of the invention may also comprise secretory signals necessary to facilitate protein secretion or other signals necessary for protein trafficking in the cell. Those skilled in the art will recognize the appropriate secretory signals.

In one embodiment the polypeptides of the invention comprise SEQ ID NO: 16 or 18. SEQ ID NO: 18 represents a (V1-Mp-Lk-V2-Hg—$C_H2$-$C_H3$)$_{(t)}$ melanocortin receptor binding alpha-MSH polypetide of generic formula (II) which has a secretory signal fused to its amino terminus. SEQ ID NO: 16 represents a (Mp-Lk-V2-Hg—$C_H2$-$C_H3$)$_{(t)}$ melanocortin receptor binding alpha-MSH polypetide of generic formula (I). No secretory signal is present in SEQ ID NO: 16. The relevant DNA and protein sequences are set forth in Tables 1A, 1B, 2A and 2B below:

TABLE 1A

Melanocortin receptor binding alpha-MSH mimetibody without secretory signal (DNA) (SEQ ID NO:15).

```
tcctactcca tggagcactt ccgctggggc aagccggtgg gatccggtgg aggctccggt   60
accttagtca ccgtctcctc agagcccaaa tcttgtgaca aaactcacac gtgcccaccg  120
tgcccagcac ctgaactcct ggggggaccg tcagtcttcc tcttcccccc aaaacccaag  180
gacaccctca tgatctcccg gacccctgag gtcacatgcg tggtggtgga cgtgagccac  240
gaagaccctg aggtcaagtt caactggtac gtggacggcg tggaggtgca taatgccaag  300
acaaagccgc gggaggagca gtacaacagc acgtaccggg tggtcagcgt cctcaccgtc  360
ctgcaccagg actggctgaa tggcaaggag tacaagtgca aggtctccaa caaagccctc  420
ccagccccca tcgagaaaac catctccaaa gccaaagggc agccccgaga accacaggtg  480
tacaccctgc cccatcccg ggatgagctg accaagaacc aggtcagcct gacctgcctg  540
gtcaaaggct tctatcccag cgacatcgcc gtggagtggg agagcaatgg gcagccggag  600
aacaactaca agaccacgcc tcccgtgctg gactccgacg gctccttctt cctctacagc  660
```

TABLE 1A-continued

Melanocortin receptor binding alpha-MSH mimetibody without secretory signal (DNA) (SEQ ID NO:15).

```
aagctcaccg tggacaagag caggtggcag caggggaacg tcttctcatg ctccgtgatg   720
catgaggctc tgcacaacca ctacacgcag aagagcctct ccctgtctcc gggtaaa     777
```

TABLE 1B

Melanocortin receptor binding alpha-MSH mimetibody without secretory signal (PROTEIN) (SEQ ID NO:16).

Ser Tyr Ser Met Glu His Phe Arg Trp Gly Lys Pro
Val Gly Ser Gly Gly Gly Ser Gly Thr Leu Val Thr
Val Ser Ser Glu Pro Lys Ser Cys Asp Lys Thr His
Thr Cys Pro Pro Cys Pro Ala Pro Glu Leu Leu Gly
Gly Pro Ser Val Phe Leu Phe Pro Pro Lys Pro Lys
Asp Thr Leu Met Ile Ser Arg Thr Pro Glu Val Thr
Cys Val Val Val Asp Val Ser His Glu Asp Pro Glu
Val Lys Phe Asn Trp Tyr Val Asp Gly Val Glu Val
His Asn Ala Lys Thr Lys Pro Arg Glu Glu Gln Tyr
Asn Ser Thr Tyr Arg Val Val Ser Val Leu Thr Val
Leu His Gln Asp Trp Leu Asn Gly Lys Glu Tyr Lys

TABLE 1B-continued

Melanocortin receptor binding alpha-MSH mimetibody without secretory signal (PROTEIN) (SEQ ID NO:16).

Cys Lys Val Ser Asn Lys Ala Leu Pro Ala Pro Ile
Glu Lys Thr Ile Ser Lys Ala Lys Gly Gln Pro Arg
Glu Pro Gln Val Tyr Thr Leu Pro Pro Ser Arg Asp
Glu Leu Thr Lys Asn Gln Val Ser Leu Thr Cys Leu
Val Lys Gly Phe Tyr Pro Ser Asp Ile Ala Val Glu
Trp Glu Ser Asn Gly Gln Pro Glu Asn Asn Tyr Lys
Thr Thr Pro Pro Val Leu Asp Ser Asp Gly Ser Phe
Phe Leu Tyr Ser Lys Leu Thr Val Asp Lys Ser Arg
Trp Gln Gln Gly Asn Val Phe Ser Cys Ser Val Met
His Glu Ala Leu His Asn His Tyr Thr Gln Lys Ser
Leu Ser Leu Ser Pro Gly Lys

TABLE 2A

Melanocortin receptor binding alpha-MSH mimetibody with secretory signal and V1 (DNA) (SEQ ID NO:17).

```
atggcttggg tgtggaccct gctattcctg atggcggccg cccaaagtat acaggcccag    60
atccagtcct actccatgga gcacttccgc tggggcaagc cggtgggatc cggtggaggc   120
tccggtacct tagtcaccgt ctcctcagag cccaaatctt gtgacaaaac tcacacgtgc   180
ccaccgtgcc cagcacctga actcctgggg ggaccgtcag tcttcctctt ccccccaaaa   240
cccaaggaca ccctcatgat ctcccggacc ccrgaggtca catgcgtggt ggtggacgtg   300
agccacgaag accctgaggt caagttcaac tggtacgtgg acggcgtgga ggtgcataat   360
gccaagacaa agccgcggga ggagcagtac aacagcacgt accgggtggt cagcgtcctc   420
accgtcctgc accaggactg gctgaatggc aaggagtaca agtgcaaggt ctccaacaaa   480
gccctcccag cccccatcga gaaaaccatc tccaaagcca agggcagccc cgagaacca   540
caggtgtaca ccctgccccc atcccgggat gagctgacca agaaccaggt cagcctgacc   600
tgcctggtca aaggcttcta tcccagcgac atcgccgtgg agtgggagag caatgggcag   660
ccggagaaca actacaagac cacgcctccc gtgctggact ccgacggctc cttcttcctc   720
tacagcaagc tcaccgtgga caagagcagg tggcagcagg gaacgtctt ctcatgctcc   780
gtgatgcatg aggctctgca caaccactac acgcagaaga gcctctccct gtctccgggt   840
aaa                                                                 843
```

TABLE 2B

Melanocortin receptor binding alpha-MSH mimetibody
with secretory signal and V1 (PROTEIN)
(SEQ ID NO:18).

Met Ala Trp Val Trp Thr Leu Leu Phe Leu Met Ala

Ala Ala Gln Ser Ile Gln Ala Gln Ile Gln Ser Tyr

Ser Met Glu His Phe Arg Trp Gly Lys Pro Val Gly

Ser Gly Gly Gly Ser Gly Thr Leu Val Thr Val Ser

Ser Glu Pro Lys Ser Cys Asp Lys Thr His Thr Cys

Pro Pro Cys Pro Ala Pro Glu Leu Leu Gly Gly Pro

Ser Val Phe Leu Phe Pro Pro Lys Pro Lys Asp Thr

Leu Met Ile Ser Arg Thr Pro Glu Val Thr Cys Val

Val Val Asp Val Ser His Glu Asp Pro Glu Val Lys

Phe Asn Trp Tyr Val Asp Gly Val Glu Val His Asn

Ala Lys Thr Lys Pro Arg Glu Glu Gln Tyr Asn Ser

Thr Tyr Arg Val Val Ser Val Leu Thr Val Leu His

Gln Asp Trp Leu Asn Gly Lys Glu Tyr Lys Cys Lys

Val Ser Asn Lys Ala Leu Pro Ala Pro Ile Glu Lys

Thr Ile Ser Lys Ala Lys Gly Gln Pro Arg Glu Pro

Gln Val Tyr Thr Leu Pro Pro Ser Arg Asp Glu Leu

Thr Lys Asn Gln Val Ser Leu Thr Cys Leu Val Lys

Gly Phe Tyr Pro Ser Asp Ile Ala Val Glu Trp Glu

Ser Asn Gly Gln Pro Glu Asn Asn Tyr Lys Thr Thr

Pro Pro Val Leu Asp Ser Asp Gly Ser Phe Phe Leu

Tyr Ser Lys Leu Thr Val Asp Lys Ser Arg Trp Gln

Gln Gly Asn Val Phe Ser Cys Ser Val Met His Glu

Ala Leu His Asn His Tyr Thr Gln Lys Ser Leu Ser

Leu Ser Pro Gly Lys

The invention also contemplates the use of polynucleotides comprising, complementary to or having significant identity with, a polynucleotide encoding at least one melanocortin receptor binding mimetibody. The invention also contemplates the use of a pharmaceutical composition comprising an effective amount of at least one mimetibody polypeptide and a pharmaceutically acceptable carrier or diluent. The term "effective amount" generally refers to the quantity of mimetibody necessary for effective therapy, i.e., the partial or complete alleviation of the symptom or disorder for which treatment was sought. The composition can optionally comprise at least one further compound, protein or composition useful for treating obesity and the other conditions described below. The pharmaceutically acceptable carrier or diluent in the compositions can be a solution, suspension, emulsion, colloid or powder. Those skilled in the art will recognize other pharmaceutically acceptable carriers and diluents.

The mimetibodies employed in the present invention are further described with reference to the following examples.

These examples are merely to illustrate aspects of the present invention and are not intended as limitations of this invention.

EXAMPLE 1

Alpha-MSH Mimetibody and Expression Vector Construction

An alpha-MSH mimetibody protein comprising a secretory signal sequence, an alpha-MSH peptide sequence, a linker sequence, $V_H$ sequence, a hinge sequence, a human IgG$_1$ $C_H2$ sequence and a human IgG$_1$ $C_H3$ sequence was designed (Tables 2A & 2B and SEQ ID NO. 18) Analytical data, e.g., mass spectroscopy, has confirmed that a mature polypeptide is generated (61,344.6 for G1/G1 form). Nucleic acid sequences encoding this alpha-MSH mimetibody protein (SEQ ID NO: 17) were generated using standard molecular biology techniques. Nucleic acid sequences encoding the alpha-MSH mimetibody sequence were subcloned into the p2389 expression vector to generate an alpha-MSH mimetibody expression vector.

EXAMPLE 2

Alpha-MSH Mimetibody Expression

The alpha-MSH mimetibody was transiently expressed in HEK293E cells. Cells were cultured using standard conditions and transiently transfected with the alpha-MSH mimetibody expression vector using Lipofectamine 2000 (Invitrogen, Carlsbad, Calif.) as directed by the manufacturer. 24 h after transfection cells were transferred to a serum free media formulation and cultured for 5 days. The culture media was then removed and centrifuged to remove debris. Clarified media was incubated with Protein A-Sepharose™ (HiTrap rProtein A FF, Amersham Biosciencies, Piscataway, N.J.) and proteins were eluted from the Protein A-Sepharose™ conjugate as directed by the manufacturer. The eluted protein solution was then further purified via Superose™ 12 size exclusion chromatography (Superose 12 10/300 GL, Amersham Biosciencies, Piscataway, N.J.) using standard methods. Column eluant was then subjected to SDS-PAGE and visualized by silver and Coomassie blue staining. Western blots were then prepared and the blots were probed with either an Fc specific primary antibody or an alpha-MSH specific primary antibody. Together, the Western Blot and SDS-PAGE staining results indicated that a purified alpha-MSH mimetibody, composed of two polypeptide chains, had been obtained from the transiently transfected HEK293 cells.

EXAMPLE 3

Alpha-MSH Mimetibody Binds MC4R

The alpha-MSH mimetibody binds to MC4R and can compete with radiolabeled [Nle(4), D-Phe(7)]-alpha-MSH (NDP-alpha-MSH) agonist molecules for MC4R binding. MC4R is a receptor for alpha-MSH. alpha-MSH binding to recombinantly expressed MC4R in HEK293 cell membranes (Perkin Elmer Life and Analytical Sciences, Boston, Mass.) was examined by competive binding assays in which increasing amounts of unlabeled MC4R agonists (positive controls) and the Fc domain of a human antibody (negative control) were added to assay cocktails containing [$^{125}$I]-NDP-alpha-MSH. The unlabeled MC4R agonists were melanotan II (MTII; an alpha MSH analog), alpha-MSH, and NDP-alpha-MSH. Alpha-MSH mimetibody binding to MC4R was stable after two weeks of storage at 4° C., −20° C., and −80° C. in PBS (phosphate buffered saline) as assessed by competive binding assays.

Competivive binding assays were performed using Scintillation Proximity Assays® (Amersham Biosciences Corp, Piscataway, N.J.) as directed by the assay manufacturer. Assay cocktails contained [$^{125}$I]-NDP-alpha-MSH at EC80, i.e., ~0.5 nM, 0.1 μg of MC4R membranes, 1 mM MgSO$_4$, 1.5 mM CaCl$_2$, 25 mM Hepes, 0.2% BSA, 1 mM 1,10-phenthroline, an assay manufacturer recommended quantity of protease inhibitor cocktail (Roche Diagnostics Corp., Indianapolis, Ind.) and SPA beads. Light emission from Scintillation Proximity Assay® beads was measured with a Packard Top Count NXT Instrument (Perkin Elmer Life and Analytical Sciences, Boston, Mass.) for 5 minutes.

Other Conjugates, Homologs and Fusions

Other exemplary melanocyte-stimulating hormone peptides include, but are not limited to, β-MSH and γ-MSH, fragments of such peptides, homologs of such peptides, mimetics (peptide or non-peptide) of such peptides, fusion proteins comprising such peptides, conjugates of such peptides, and any pharmaceutical salts of such peptides.

Systems and Methods

In one embodiment, the method of the present invention is particularly useful for treating obesity. The methods and compositions of the invention can be used to reduce, ameliorate, or prevent obesity in a subject that suffers from obesity, or is at risk of developing obesity.

According to one aspect of the invention, implantable drug infusion pumps are used to provide site specific and/or sustained delivery of the appetite suppressing agents to a localized region of the subject. The pumps can be used for the continuous or periodic delivery over relatively long periods of time. The implantable pumps ensures that the appetite suppressing agent is delivered to the target site in the central nervous system (e.g., the brain), at a concentration and for a duration effective to cause a therapeutic effect.

A variety of known implantable drug infusion pumps can be used to deliver the appetite suppressing agent according to the present invention. Suitable infusion pumps must be capable of delivering a drug to a site within the central nervous system, such as the brain or the intrathecal space, over an extend period of time. Suitable pumps include those that continuously deliver the drug at a selected flow rate, those that deliver the drug at a flow rate according to a programmed or programmable protocol, those that deliver the drug based on sensed physiological parameters and those that deliver the drug at an adjustable flow rate. Exemplary infusion pumps include those having osmotic pumps, pressure driven pumps, motorized pumps, and others known to those skilled in the art.

An implantable delivery pump according to the present invention may include, for example, an implantable osmotic delivery pump as described in U.S. Pat. Nos. 5,728,396, 5,985,305, 6,113,938, 6,132,420, 6,156,331, 6,375,978, 6,395,292, the contents of each of which are incorporated herein in their entirety by reference. An implantable pump according to the present invention may also include a regulator-type implantable pump that provides constant flow, adjustable flow, or programmable flow of appetite suppressing agent formulations. Examples of non-osmotic implantable pumps that may be included in an implantable pump of the present invention include those pumps described in U.S. Pat. Nos. 5,713,847, 5,368,588, 6,436,091, 6,447,522, and 6,248,112, the contents of each of which are incorporated herein in their entirety by reference. Other implantable pumps are disclosed in U.S. Pat. Nos. 5,034,229, 5,057,318, and 5,110,596, the contents of which are incorporated herein by reference. Further examples of implantable pumps are described in U.S. Pat. Nos. 6,283,949, 5,976,109, 5,836,935, 5,511,355, which are incorporated herein by reference.

Formulations

The appetite suppressing agent can be formulated as a stable suspension suitable for delivery by an implantable infusion pump to a site within the central nervous system. In particular, the appetite suppressing agent can be formulated such that it is stable at ambient and physiological temperatures. In one embodiment, the appetite suppressing agent is a melanocortin protein or peptide fragment thereof. Peptides and proteins are naturally active in aqueous environments, however, peptide and protein stability is often a problem in aqueous formulations used for long durations of time at ambient or physiological temperatures. Peptides and proteins are unstable and tend to degrade via a number of mechanisms, including deamidation, oxidation, hydrolysis, disulfide interchange, and racemization.

One method for providing peptide and protein formulations that are stable over time at ambient or physiological temperatures, conjugating the peptide or protein to an antibody or an antibody fragment, to provide a stable antibody-appetite suppressing peptide conjugate, as described herein and in more detail in U.S. application No. 60/637,818, incorporated herein by reference. This appetite suppressing antibody-peptide conjugate (mimetibody) can then be formulated into a stable suspension for delivery by an implantable pump.

Suitable stable suspensions of the appetite suppressing peptide or mimetobody can be formulated in an excipient such water, saline, phosphate buffered solutions, Ringer's solution, dextrose solution, Hank's solution, polyethylene glycol-containing physiologically balanced salt solutions, and other aqueous, physiologically balanced, salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Preferably MSH mimetibodies would be in formulations of Phosphate buffer solution or saline. Concentrations of up to 30 mg/ml have been observed in both solutions without any observable change in integrity and activity of the protein.

One skilled in the art will recognize that excipients can also contain minor amounts of additives, such as substances that enhance isotonicity and chemical stability, or buffers. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration Other techniques for producing a stable formulation for delivery via an implantable infusion pump, according to the invention, include suspending the appetite suppressing agent in a vehicle such as a non-aqueous vehicle, an anhydrous vehicle, an aprotic vehicle, a hydrophobic vehicle, a non-polar vehicle, a non-aqueous vehicle, a protic vehicle, an anhydrous psuedoplastic and thixotropic oleaginous vehicle, a liposomal vehicle, and a cationic lipid vehicle.

Maintaining a substantially uniform dispersion of appetite suppressing agent over time facilitates controlled delivery of the appetite suppressing agent from an implanted pump. It is important that the appetite suppressing agent remain uniformly dispersed within a suspension that is loaded into an implantable infusion pump. A lack of uniform dispersion may result in a non-uniform amount of appetite suppressing agent being delivered to the target site, which may cause the amount of appetite suppressing agent delivered from the implanted pump to exceed recommended dosing regimens or, alternatively, cause the amount of appetite suppressing agent delivered to fall below therapeutic levels.

In one embodiment, a substantially uniform dispersion of appetite suppressing agent is maintained by incorporating high viscosity material within the suspension. Exemplary viscosity enhancing materials include polymers, such as olyvinylpyrrolidone, may be used to provide suspension vehicles that not only allow the formulation of the appetite suppressing agent suspensions that are stable over time, but also offer the viscosity required to maintain a substantially uniform dispersion of agent. To achieve high viscosity vehicles using polymer materials, the polymer may be dissolved in a non-aqueous solvent to create single phase, viscous solution.

The formulations may comprise the appetite suppressing agent with about 0.1% to 90% by weight of the agent, about 0.1% to about 50%, about 0.1% to about 25%, about 0.1% to about 10%, and about 0.1% to 1.0% by weight of the agent.

In accordance with the present invention, a suitable or effective single dose size is a dose that is capable of causing a measurable change in the body weight (e.g., a decrease in body weight) of a subject when administered one or more times over a suitable time period. Doses can vary depending upon the condition of the subject being treated, including the apparent cause of the body weight problem and/or any other related or non-related health factors experienced by a particular subject.

In one embodiment, the invention comprises delivering an appetite suppressing agent, e.g., a melanocortin at a dose, concentration, and for a time sufficient to cause a measurable change in the body weight or mass of the subject. The dose of the melanocortin can be between about 0.1 µg and about 100 mg per kilogram body weight of the subject; between about 0.1 µg and about 10 mg per kilogram body weight of the subject; between about 0.1 µg and about 1 pg per kilogram body weight of the subject; and between about 1 µg and about 10 mg per kilogram body weight of the subject. A typical daily dose for an adult human (i.e., a 75 kg human) is from about 1 milligram to about 100 milligrams. In practicing this method, the appetite suppressing agent or therapeutic formulation containing the appetite suppressing agent can be administered in a single daily dose or in multiple doses per day. This treatment method may require administration over extended periods of time. The amount per administered dose or the total amount administered will be determined by the physician and will depend on such factors as the mass of the subject, the age and general health of the subject and the tolerance of the subject to the compound.

In one embodiment, the appetite suppressing agent can be delivered alone or in combination with another agent, such as another appetite suppressing agent, e.g., leptin and/or neuropeptin Y. In another embodiment, the appetite suppressing agent can be delivered in combination with another therapeutic agent, such as a pain controlling agent.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The prefer sites in the brain would be hypothalamus, specifically paraventricular nucleus and ventro-medical nucleus of hypothalamus. In addition, nucleus of solitary tract would be also of benefit. Above listed nuclei are the known centers for regulation of energy balance that have high level of expression of MC4 and MC3 receptors.

What is claimed:

1. A method of suppressing appetite comprising:
implanting a drug infusion pump into a site in a subject; and delivering a stable suspension of an effective dosage of an appetite suppressing agent to a site in a central nervous system of the subject, the appetite suppressing agent comprising a polypeptide having the general formula:

(Mp-Lk-V2—Hg—$C_H2$—$C_H3$)$_{(t)}$ wherein Mp is an alpha melanocyte-stimulating hormone (α-MSH) peptide, LK is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region, $C_H3$ is an immunoglobulin heavy chain $C_H3$ constant region, and t is an integer of 1 to 10, wherein the appetite suppressing agent binds to a target receptor on a neural cell in the central nervous system and modifies the receptor function to suppress appetite.

2. The method of claim 1, wherein the target receptor is a melanocortin receptor selected from the group consisting of melanocortin-1 receptor (MC1R), melanocortin-2 receptor (MC2R), melanocortin-3 receptor (MC3R), melanocortin-4 receptor (MC4R), and melanocortin-5 receptor (MC5R).

3. The method of claim 1, wherein the target receptor is melanocortin-4 receptor (MC4R).

4. The method of claim 1, wherein the target is melanocortin-3 receptor (MC3R).

5. The method of claim 1, wherein the site in the central nervous system is the brain.

6. The method of claim 1, further comprising delivering a second appetite suppressing agent selected from the group consisting of leptin, NPY peptide, antagonist, PYY 3-36 peptide agonist or its analog, GLP-1 peptide or its analog and MCH receptor antagonist.

7. A method for ameliorating obesity in a subject, comprising:
implanting a drug infusion pump into a site in a subject; and delivering a stable suspension of an appetite suppressing agent to a region in a central nervous system of the subject, appetite suppressing agent comprising a polypeptide having the general formula:

(Mp-Lk-V2—Hg—$C_H2$—$C_H3$)$_{(t)}$ wherein Mp is an alpha melanocyte-stimulating hormone (α-MSH) peptide, LK is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region $C_H3$ is an immunoglobulin heavy chain $C_H3$ constant region, and t is an integer of 1 to 10, wherein the appetite suppressing agent binds to a melanocortin receptor on a neural cell in the central nervous system and modifies the melanocortin receptor function to suppress appetite, thereby ameliorating obesity.

8. The method of claim 7, wherein the target receptor is a melanocortin receptor selected from the group consisting of melanocortin-1 receptor (MC1R), melanocortin-2 receptor (MC2R), melanocortin-3 receptor (MC3R), melanocortin-4 receptor (MC4R), and melanocortin-5 receptor (MC5R).

9. The method of claim 7, wherein the target receptor is melanocortin-4 receptor (MC4R).

10. The method of claim 7, wherein the target receptor is melanocortin-3 receptor (MC3R).

11. The method of claim 7, wherein the region in the central nervous system is the brain.

12. The method of claim 7, further comprising delivering a second appetite suppressing agent selected from the group consisting of leptin, NY peptide antagonist, PYY 3-36 peptide agonist or its analog, GLP-1 peptide or its analog, and MCH receptor antagonist.

\* \* \* \* \*